United States Patent [19]

O'Neill

[11] 4,436,519

[45] Mar. 13, 1984

[54] REMOVABLE HEMOSTASIS VALVE

[75] Inventor: William J. O'Neill, Garland, Tex.

[73] Assignee: Argon Medical Corp., Athens, Tex.

[21] Appl. No.: 267,984

[22] Filed: May 28, 1981

[51] Int. Cl.³ .............................................. A61M 5/00
[52] U.S. Cl. ..................................... 604/175; 604/256
[58] Field of Search ........... 128/1 R, 348, 274, 214 R, 128/247, 214.4; 137/846, 847; 215/341, 351, 354–355; 220/DIG. 19; 251/149.1, 149.9; 604/99, 169, 175, 256

[56] References Cited

U.S. PATENT DOCUMENTS

| | | |
|---|---|---|
| 3,459,188 | 8/1969 | Roberts . |
| 3,547,119 | 12/1970 | Hall et al. . |
| 3,592,192 | 7/1971 | Harautuncian . |
| 3,977,400 | 8/1976 | Moorehead . |
| 4,000,739 | 1/1977 | Stevens . |
| 4,013,310 | 3/1977 | Oye .................................... 128/247 |
| 4,079,738 | 3/1978 | Dunn et al. . |
| 4,106,506 | 8/1978 | Koehn . |
| 4,149,535 | 4/1979 | Volder . |
| 4,164,221 | 8/1979 | Bentley et al. ...................... 128/348 |
| 4,269,186 | 5/1981 | Loveless et al. ................. 128/214.4 |

*Primary Examiner*—Richard J. Apley
*Assistant Examiner*—George Yanulis
*Attorney, Agent, or Firm*—Lawrence S. Levinson; Sanford J. Asman

[57] ABSTRACT

A homostasis valve comprising a body having a central passage, a seal having a central aperature therein, the seal being mounted in the central passage, and a diaphragm having a wall member with a slit therein, the diaphragm being mounted in the central passage, the diaphragm wall member having an inner bottom diaphragm surface, and an outer bottom diaphragm surface, the slit extending from the inner bottom diaphragm surface to the outer bottom diaphragm surface, the wall member having a diaphragm chamber therewithin.

10 Claims, 5 Drawing Figures

REMOVABLE HEMOSTASIS VALVE

BACKGROUND OF THE INVENTION

Stevens in U.S. Pat. No. 4,000,739 discloses a hemostasis cannula comprising a body having a passage therethrough adapted to receive a catheter and a pair of juxtaposed gaskets mounted in the passage. The first gasket forms a seal around a catheter enclosed within the cannula. The second gasket is compressed against the first to seal the passage when the catheter is removed. The cannula also features a flexible entrance to and a port for introducing fluids into the patient's blood vessel.

SUMMARY OF THE INVENTION

The invention relates to a hemostasis valve comprising a body having a central passage, a seal having a central aperature therein, the seal being mounted in the central passage, and a diaphragm having a wall member with a slit therein, the diaphragm being mounted in the central passage, the diaphragm wall member having an inner bottom diaphragm surface, and an outer bottom diaphragm surface, the slit extending from the inner bottom diaphragm surface to the outer bottom diaphragm surface, the wall member having a diaphragm chamber therewithin.

The central portion of the valve body has a passage therethrough. This central passage is discussed with reference to its upper and lower portions. The upper central passage 59 has diaphragm 5 mounted therein. The lower central passage serves to guide and support the catheter used in conjunction with hemostasis valve.

DETAILED DESCRIPTION OF THE DRAWING

Figure 1:
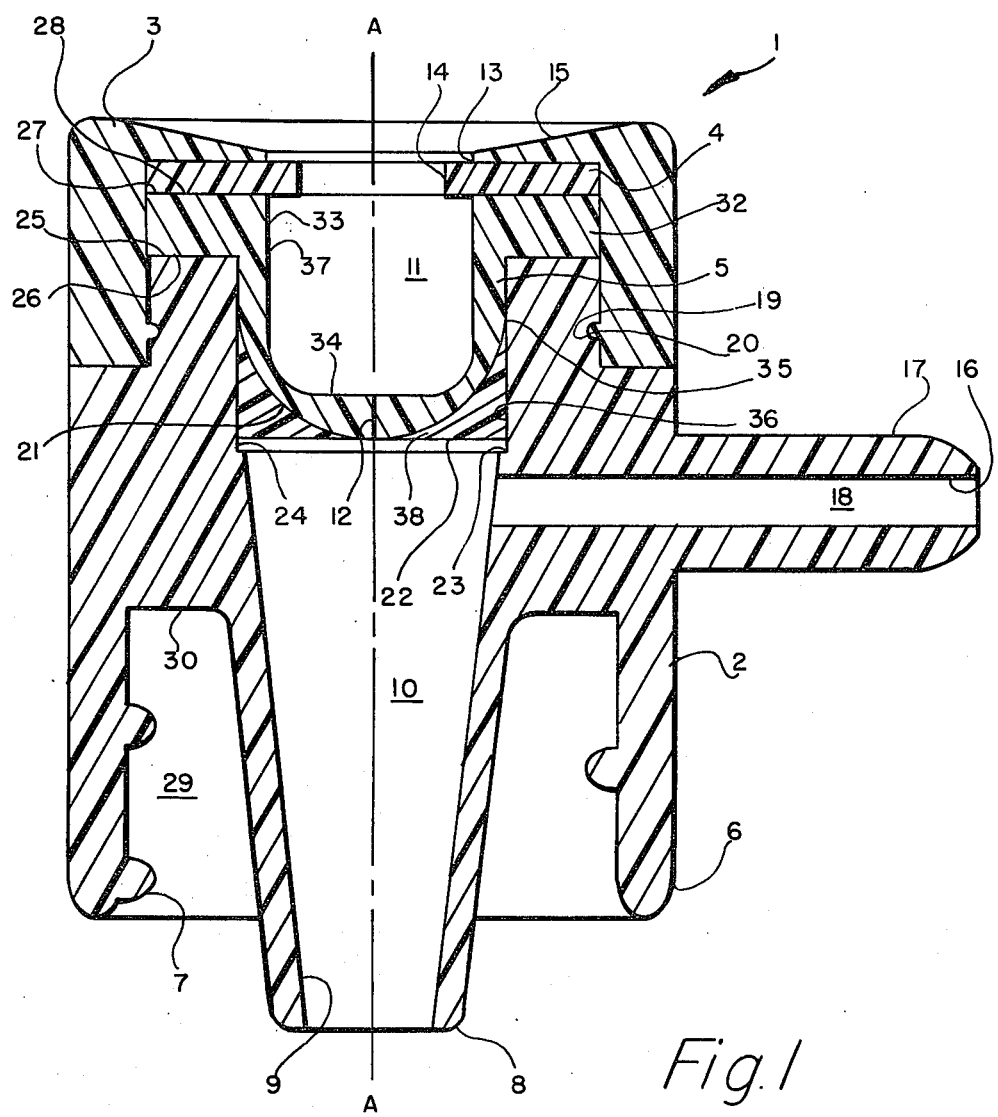
FIG. 1 is a cross-sectional view of a hemostasis valve in accordance with the present invention.
Figure 3:
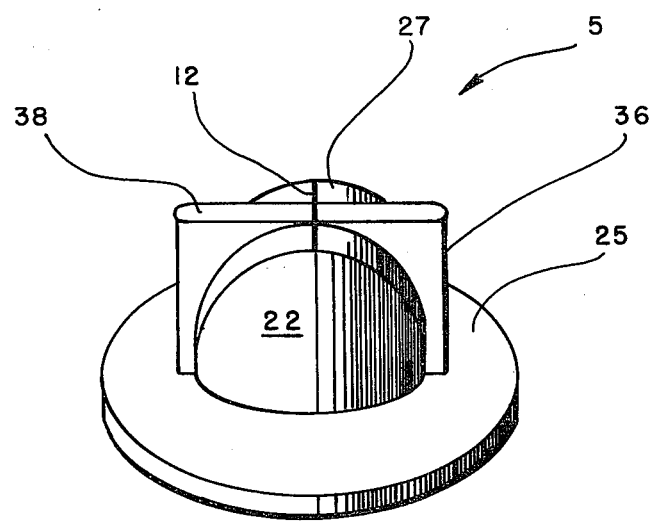
FIG. 3 is a perspective view of one embodiment of the self-closing isolation diaphragm of the present invention.
Figure 4:
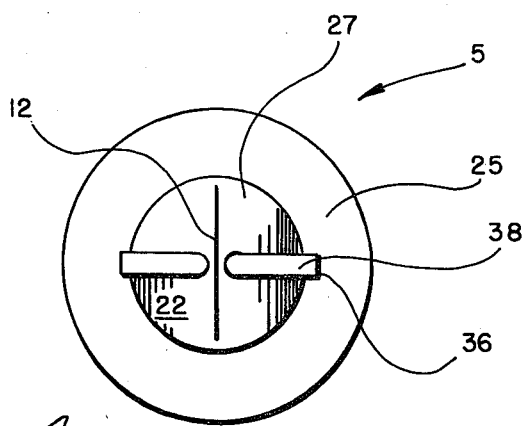
FIG. 4 is a bottom view of the diaphragm of FIG. 3.
Figure 5:
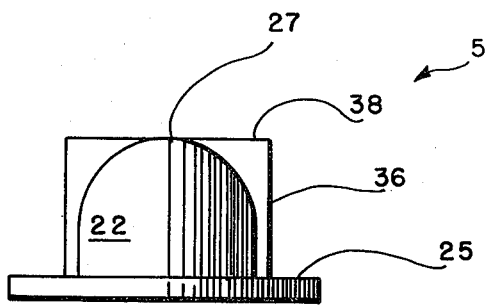
FIG. 5 is a side view of the diaphragm of FIG. 3.

FIG. 1 is a cross-sectional view of a valve in accordance with the invention. The hemostasis valve is shown generally at 1. The valve housing 2 has a retaining cap 3 thereover. The retaining cap 3 is preferably made of plastic. A catheter seal 4 is held in place by the retaining cap 3. A self-closing isolation diaphragm 5 has diaphragm upper flange surface 27 which is in contact with catheter seal lower surface 28. The self-closing isolation diaphragm 5 has diaphragm wall member 37. The diaphragm wall member 37 has diaphragm inner side surface 33, diaphragm outer bottom surface 21 and diaphragm inner bottom surface 34. The self-closing isolation diaphragm chamber 11 is bounded by diaphragm inner side surface 33 and diaphragm inner bottom surface 34. The self-closing isolation diaphragm flange 32 has diaphragm lower flange surface 25 which is in contact with valve housing top surface 26. The retaining cap provides fluid-tight sealing by its tight retention with retaining cap rib 20 which fits into valve housing groove 19. The fit between the retaining cap 3, catheter seal 4 and the self-closing isolation diaphragm flange 32 is such that the catheter seal 4 and the diaphragm flange 32 are compressed by the retaining cap 3. The catheter seal 4 and the diaphragm flange 32 are held in compression by the retaining cap rib 20. The retaining cap 3 is provided with retaining cap beveled surface 15 which slopes into retaining cap aperture 13 through which a catheter tube may be inserted. The catheter seal 4 is provided with catheter seal aperture 14. Thus, when a catheter is inserted through the valve it would extend through the retaining cap aperture 13, the catheter seal aperture 14 and the self-closing isolation diaphragm chamber 11 whereupon it would meet the diaphragm inner bottom surface 34 at the diaphragm slit 12. The slit 12 opens to allow passage of the catheter being inserted and the catheter passses into and through the lower central passage 10. The lower central passage inner surface 9 provides support for the catheter. The self-closing isolation diaphragm 5 is provided with a diaphragm outer side surface 35. The surface 35 is integrally connected therewith diaphragm rib 38. The diaphragm rib 38 has a diaphragm rib side surface 36 and diaphragm rib bottom surface 22, as shown in FIGS. 3, 4 and 5.

Figure 2:
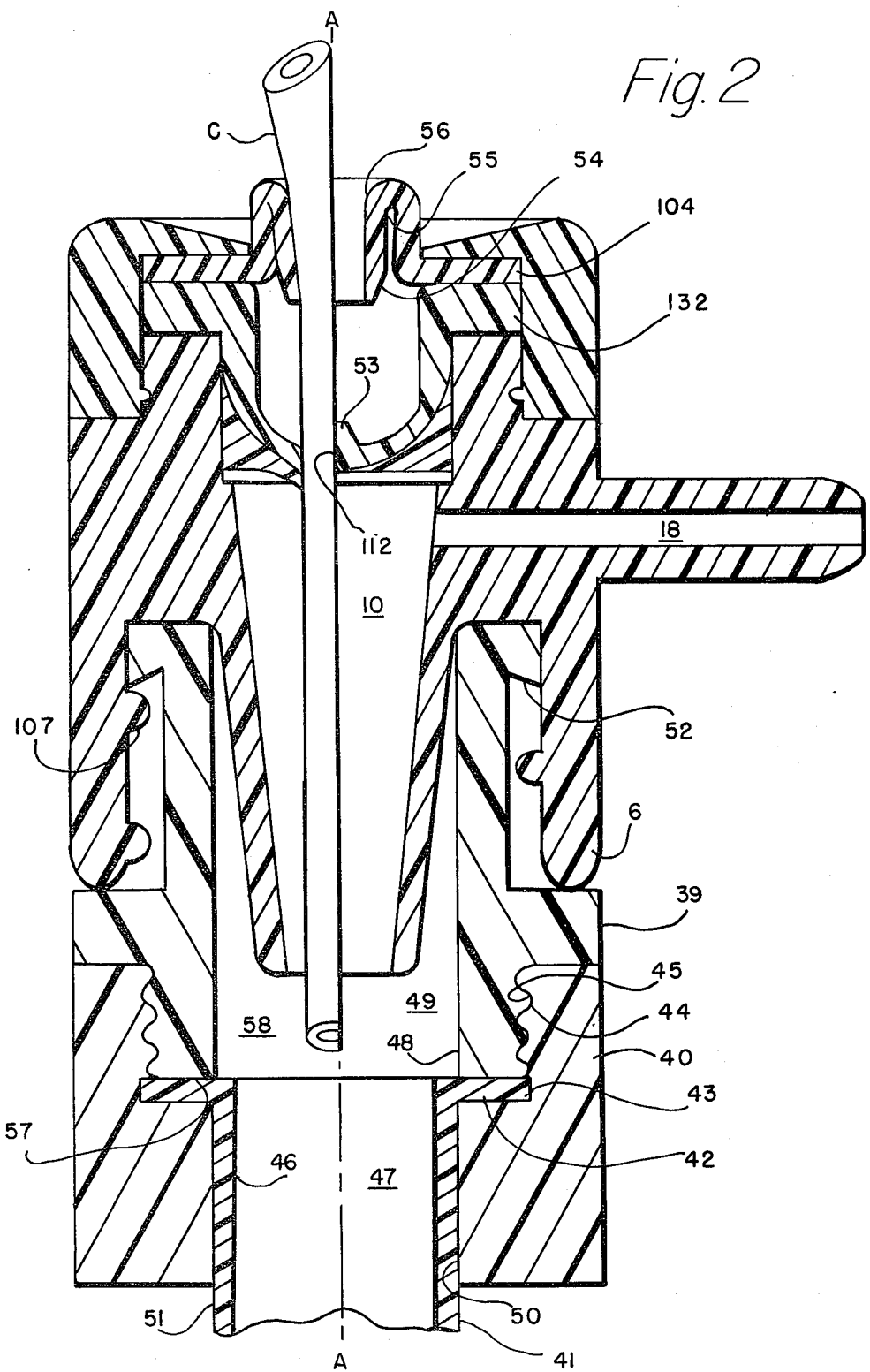
FIG. 2 is a cross-sectional view of a preferred embodiment of the invention with and without a catheter inserted.

Upon forcing the catheter through the diaphragm slit 12, the diaphragm rib 38 compresses against the upper central passage wall 24. Upon withdrawing the catheter from the hemostasis valve 1 the compressed diaphragm rib 38 expands to its original position, causing the diaphragm slit 12 to close. The hemostasis valve 1 is provided with fast release connector 6. The fast release connector threads 7 are available to connect the valve to fast connect fastener flange 52 as shown in FIG. 2. The connector chamber wall 30 surrounds a connector chamber 29. The hemostasis valve is further provided with a side passage 18. The side passage 18 has side passage inner surface 16. Side passage outer surface 17 extends outwardly from the valve housing 2. The fast connect fastener 39 has fast connect fastener flange 52 which rides on threads 107 of the valve. Fast connect fastener passage 49 has fast connect passage inner surface 48 through which the catheter C passes, as shown in FIG. 2. The tubing 41 has tubing flange 43 which holds the tubing 41 to the fast connect fastener 39. The fastener cap 40 has fastener cap threads 44 which are threaded onto fast connect fastener threads 45. As the fastener cap 40 is threaded onto the fast connect fastener 39 the fastener cap flange 42 compresses the tubing flange 43 against the lower fast connect fastener surface 57. The tubing 41 has a tubing passage inner wall 46 which surrounds the tubing passage 47. The tubing 41 has a tubing passage outer surface 51 which is supported at its upper end by fastener cap inner surface 50.

FIG. 2 shows cushion seal 104 having a cushion lip outer curved surface 56, a cushion lip inner curved surface 55. The cushion lip inner curved surface 55 has cushion lip beveled surface 54 which is in contact with lipped diaphragm 132. Lipped diaphragm 132 has diaphragm lip 53. The lower central passage of the fast release connector has a central axis A—A as shown in FIG. 1. The fast release connector 6 is concentric with the lower central passage 10. The fast release connector is coaxial with the lower central passage 10.

As shown in FIG. 2 when a catheter C is inserted into the cushion seal the cushion lip outer curved surface flexibly supports the catheter. As the catheter passes through the slit 112 of the lipped diaphragm 132 the diaphragm lip 53 is carried downwardly into the lower central passage 10. Upon further insertion the catheter passes through the fast connect fastener passage 49 and into the tubing passage 47.

In use fluids may be transferred through the catheter C into the blood vessel of the patient. The hemostasis valve is operable for easy entry of the catheter C and yet provides for positive closing as the catheter C is removed. The diaphragm prevents any leakage either inward or outward with applied pressures to as high as 500 mm Hg. The hemostasis valve is operable so that the tubing 41 may be separated from the valve housing 2, leaving the tubing in place. This allows for replacing the valve housing 2 in case it is damaged or contaminated. This makes it unnecessary to prepare a new entry site in the patient. FIG. 2 shows a preferred embodiment of the invention with a cushioned seal which prevents leakage even when the catheter C is displaced to one side.

FIG. 2 shows a cross-sectional view of a preferred embodiment of the invention. To the left of the center line the embodiment is shown with the catheter inserted. To the right of the center line the embodiment is shown without the catheter inserted.

In use the fluid is fed through side passage 18 from a bag of fluid which may be suspended on a pole next to the patient. The fluids may contain antibiotics, nutrients, or any suitable liquid useful for intravenous passage into the patient. From the side passage 18, the fluid travels into and downwardly in the central passage 58 by first passing through the lower central passage 10. The fluid continues downwardly through the fast connect fastener passage 49 and into the tubing passage 47. The tubing 41 having previously been inserted into the patient's vessel. The insertion of the tubing 41 into the patient's vessel may be done as is known in the art. For example, the patient's vessel may be opened by cutting followed by insertion of a string dilator. Into the string dilator is inserted the tubing 41.

In using the hemostasis valve 1 in conjunction with the tubing 41 after it has been inserted into a vessel of the patient with fast connect fastener 39 attached to the end of tubing 41, the hemostasis valve 1 may be connected to the fast connect fastener 39.

When the valve 1 is connected, a just mentioned, a catheter may be inserted ss partially shown in FIG. 2 to the left side of the center line. The path followed by the catheter provides for versatility of access to the patient's vessel by catheters of various sizes and lengths and curvatures. Additionally, this path may be used for high volume of fluid delivery to the patient's vessel by using a large diameter tubular catheter to convey fluids therethrough.

When several different catheters have been inserted in the patient's vessel, they may be passed through the self-closing isolation diaphragm 5 and the catheter seal 4 into the lower central passage 10 and on downwardly as previously discussed. In place, the self-closing isolation diaphragm 5, provides fluid tight sealing around the catheter so that leakage does not occur. Upon removing the catheter, the self-closing isolation diaphragm 5 seals the upper-central passage 59 so that blood or other fluids from the lower central passage 10 are not lost or contaminated. The diaphragm wall member 37 preferably has a dome shape as shown in FIG. 1 and FIG. 2. Inherent in this shape, is the support needed to seal the slit 12 while resisting fluid pressure in lower central passage 10 and upper central passage 59. The diaphragm rib 38 assists in maintaining fluid-tight sealing around the catheter C while it is inserted through the self-closing diaphram 5. The diaphram rib 38 also helps to return the self-closing diaphram 5 to its closed position with the slit 12 closed after the catheter C is withdrawn from the valve 1.

The self-closing isolation diaphram 5 is preferably made of a flexible material such as natural or synthetic rubber. Similarly, the catheter seal 4 is preferably made of natural or synthetic rubber.

The invention may be embodied in other specific forms without departing from its spirit and essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. A hemostasis valve comprising:
   (a) a body having a central passage therein;
   (b) a seal having a central aperture therein, said seal being mounted in said central passage; and
   (c) a resilient, dome shaped diaphragm having a wall member with a single, linear slit therein, said diaphragm being mounted in said central passage, said diaphragm wall member having an inner bottom diaphragm surface, and an outer bottom diaphragm surface, said slit extending through said wall member from said inner bottom diaphragm surface to said outer bottom diaphragm surface, said wall member defining with said seal a diaphragm chamber within the space between said inner bottom diaphragm surface and said seal, whereby the side walls of said dome shaped diaphragm will act in cooperation with the walls of said central passage to resiliently urge said slit closed when no catheter is present therethrough.

2. The valve of claim 1 wherein said diaphragm further comprises a flange; and wherein said seal comprises a lower seal surface, said flange having an upper surface which is in contact with said lower seal surface.

3. The valve of claims 1 or 2 wherein said diaphragm further comprises at least one rib, said at least one rib being elongated and being perpendicularly oriented with respect to said slit, whereby said at least one rib acts to close said slit when no catheter is present therethrough.

4. The valve of claim 2 wherein said diaphragm further comprises at least one rib, each said rib being integrally connected to said outer bottom diaphragm surface, said at least one rib being elongated and being perpendicularly oriented with respect to said slit, whereby said at least one rib acts to close said slit when no catheter is present therethrough.

5. The valve of claim 1 or 2 further comprising a fast release connector.

6. The valve of claim 1 further comprising a fast release connector, and wherein said central passage comprises a lower central passage having a central axis, said connector being threaded, and having a central axis which is coaxial with the central axis of said lower central passage.

7. In a hemostasis valve comprising a body and a diaphragm having a wall member with a slit therein, said body having a central passage, the improvement wherein said valve comprises fast release connector means.

8. The valve of claim 7 wherein said connector means comprises threads.

9. A diaphragm for a self-sealing valve comprising a piece of resilient material having a dome shaped wall member, said wall member having an inner bottom surface, and an outer bottom surface, there being a single, linear slit extending through said wall member from said inner bottom surface to said outer bottom surface, said diaphragm further comprising a pair of elongated ribs on said outer bottom surface, said ribs being perpendicular to said elongated slit, whereby the resilience of said ribs acts to close said slit.

10. The diaphragm of claim 9 in which said resilient material is comprised of rubber.

* * * * *

UNITED STATES PATENT AND TRADEMARK OFFICE
CERTIFICATE OF CORRECTION

PATENT NO.   : 4,436,519
DATED        : March 13, 1984
INVENTOR(S)  : William J. O'Neill It is certified that error appears in the above-identified patent and that said Letters Patent are hereby corrected as shown below:

In the Abstract, the first line, change "homostasis" to --hemostasis--

In the Detailed Description of the Drawing, Column 2 line 15 change "passses" to --passes--

In the Detailed Description of the Drawing, Column 3 line 46, change "ss" to --as--

Signed and Sealed this

Tenth Day of March, 1987

Attest:

DONALD J. QUIGG

*Attesting Officer*    *Commissioner of Patents and Trademarks*

REEXAMINATION CERTIFICATE (1030th)
United States Patent [19]

O'Neill

[11] B1 4,436,519
[45] Certificate Issued Apr. 4, 1989

[54] REMOVABLE HEMOSTASIS VALVE

[75] Inventor: William J. O'Neill, Garland, Tex.

[73] Assignee: Argon Medical Corp., Athens, Tex.

Reexamination Request:
No. 90/000,564, May 29, 1984

Reexamination Certificate for:
Patent No.: 4,436,519
Issued: Mar. 13, 1984
Appl. No.: 267,984
Filed: May 28, 1981

[51] Int. Cl.⁴ ............................................. A61M 5/00
[52] U.S. Cl. ............................... 604/175; 604/256
[58] Field of Search ............... 604/175, 99, 169, 256;
220/DIG. 19; 251/149.1, 149.9; 137/493, 846, 847

[56] References Cited

U.S. PATENT DOCUMENTS

| | | |
|---|---|---|
| 996,588 | 6/1911 | Kennedy . |
| 1,051,554 | 1/1913 | Champion . |
| 2,674,318 | 4/1954 | Sutcliff . |
| 3,459,188 | 8/1969 | Roberts . |
| 3,504,699 | 4/1970 | Grice . |
| 3,517,682 | 6/1970 | Smith . |
| 3,547,119 | 12/1970 | Hasu et al. . |
| 3,572,375 | 3/1971 | Rosenberg . |
| 3,592,192 | 7/1971 | Harautuncian . |
| 3,710,942 | 1/1973 | Rosenberg . |
| 3,977,192 | 7/1976 | Moorehead . |
| 4,000,739 | 1/1977 | Stevens ....................... 604/280 |
| 4,013,310 | 3/1977 | Oye . |
| 4,079,738 | 3/1978 | Dunn et al. . |
| 4,106,506 | 8/1978 | Koehn . |
| 4,143,853 | 3/1979 | Abramson . |
| 4,149,535 | 4/1979 | Volder . |
| 4,164,221 | 8/1979 | Bentley . |
| 4,269,186 | 5/1981 | Loveless et al. . |
| 4,431,239 | 7/1982 | Atkinson . |

FOREIGN PATENT DOCUMENTS

| | | |
|---|---|---|
| 140567 | 4/1951 | Australia . |
| 737249 | 6/1966 | Canada . |

OTHER PUBLICATIONS

Exhibit A–Catheter Check Valve Drawing, Vernay Laboratories, Inc., 2/22/80.

Primary Examiner—Stephen C. Pellegrino

[57] ABSTRACT

A homostasis valve comprising a body having a central passage, a seal having a central aperature therein, the seal being mounted in the central passage, and a diaphragm having a wall member with a slit therein, the diaphragm being mounted in the central passage, the diaphragm wall member having an inner bottom diaphragm surface, and an outer bottom diaphragm surface, the slit extending from the inner bottom diaphragm surface to the outer bottom diaphragm surface, the wall member having a diaphragm chamber therewithin.

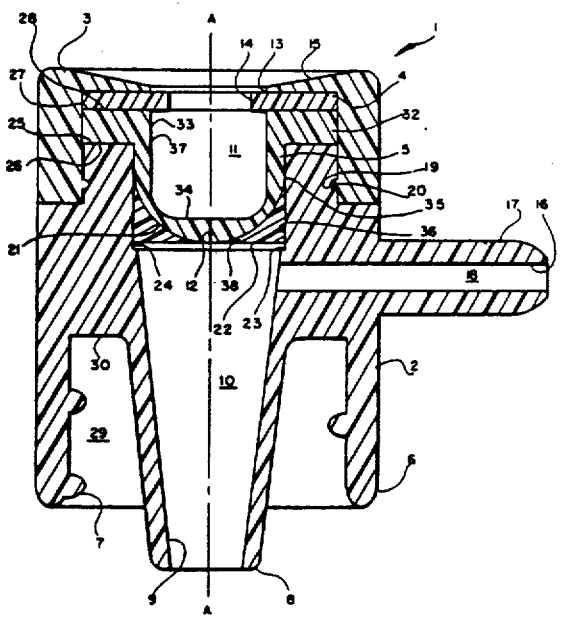

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

Claims 1-10 are cancelled.